US006478755B2

(12) United States Patent
Young

(10) Patent No.: US 6,478,755 B2
(45) Date of Patent: Nov. 12, 2002

(54) PORTABLE MASSAGER

(75) Inventor: James V. Young, University City, MO (US)

(73) Assignee: General Physiotheraphy, Earth City, MO (US)

( * ) Notice: Subject to any disclaimer, the term of this patent is extended or adjusted under 35 U.S.C. 154(b) by 0 days.

(21) Appl. No.: 08/972,706

(22) Filed: Nov. 18, 1997

(65) Prior Publication Data

US 2002/0115947 A1 Aug. 22, 2002

(51) Int. Cl.[7] ................................................ A61M 1/00
(52) U.S. Cl. .............................. 601/72; 601/69; 601/67
(58) Field of Search .............................. 601/67–70, 80, 601/72, 73, 89, 93, 134, 136, 138, 82, 83, 84, 97, 101, 107–111, 112–114; 15/22.2, 22.4, 23, 24, 28, 29, 22.1; 74/86–87; 366/123

(56) References Cited

U.S. PATENT DOCUMENTS

| | | | | | |
|---|---|---|---|---|---|
| 2,138,815 | A | | 12/1938 | Eberly | |
| 3,468,304 | A | * | 9/1969 | Teranishi | |
| 3,563,233 | A | | 2/1971 | Bodine | |
| 3,585,990 | A | | 6/1971 | Blachly et al. | 128/36 |
| 4,025,809 | A | | 5/1977 | Teranishi | 301/81 |
| 4,048,989 | A | | 9/1977 | Schaefer | |
| 4,098,266 | A | | 7/1978 | Muchisky | |
| 4,102,334 | A | | 7/1978 | Muchisky | |
| 4,162,675 | A | * | 7/1979 | Kawada | 128/55 |
| 4,224,932 | A | * | 9/1980 | Farb | 601/72 |
| 4,526,049 | A | * | 7/1985 | Pottgens | 74/87 |
| 4,757,806 | A | | 7/1988 | Muchisky | |
| 4,825,853 | A | * | 5/1989 | Iwamoto et al. | |
| 4,846,158 | A | * | 7/1989 | Teranishi | |
| 4,919,117 | A | | 4/1990 | Muchisky | |
| 4,958,628 | A | * | 9/1990 | Iwamoto et al. | |
| 5,117,815 | A | * | 6/1992 | Gentry et al. | |
| 5,125,398 | A | | 6/1992 | Horton | 128/32 |
| 5,193,528 | A | * | 3/1993 | Iwamoto et al. | |
| 5,470,303 | A | * | 11/1995 | Leonard et al. | 601/84 |
| 5,471,695 | A | * | 12/1995 | Aiyar | 601/72 X |
| D367,712 | S | | 3/1996 | Young | |
| D373,640 | S | | 9/1996 | Young | |
| 5,716,332 | A | | 2/1998 | Noble | 601/108 |
| 5,925,002 | A | | 7/1999 | Wollman | 601/70 |

FOREIGN PATENT DOCUMENTS

| | | |
|---|---|---|
| DE | 1136055 | 9/1962 |

* cited by examiner

*Primary Examiner*—Justine R. Yu
(74) *Attorney, Agent, or Firm*—Polster, Lieder, Woodruff & Lucchesi

(57) ABSTRACT

A hand held massage unit used for therapeutic purposes such as to loosen and mobilize bronchial secretions in patients, to improve blood circulation, and to relax muscles. The massage unit includes a vibration-free motor unit having a rotating output shaft directly connected to a vibratory head assembly. The rotational motion of the output shaft is transformed into oscillating orbital motion about the shaft centerline in the adapter portion of the vibratory head assembly through an offset cam integrally formed as part of a counterbalanced eccentric. Counterweights within the eccentric reduce the vibrations transmitted to the user's hand and isolate the oscillating vibration of the vibratory head assembly. Undesired rotation of the vibratory head assembly is prevented by a mounting construction between the oscillating adapter components and a stationary portion of the vibratory head assembly secured to the motor unit.

17 Claims, 5 Drawing Sheets

PORTABLE MASSAGER

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to medical devices in which medical benefits are achieved through the application of vibratory force to a patient's body. More particularly, the present invention is a portable hand-held massage unit which may be used to loosen and to mobilize bronchial secretions in the patient's body, or used to apply force to various parts of a body such as the legs, to improve the circulation of blood, mobilize edema fluids, or to relax muscles, while simultaneously reducing the level of vibration felt by the user holding the unit.

In the prior art, various methods and devices have been employed for these purposes. One method used to loosen bronchial secretions is hand massage and percussion. Hand massage techniques require a nurse or other attendant to use his or her hands to strike the back or chest of the patient to cause a loosening of secretions within the patient's lungs. This can be painful, and may result in broken ribs or severe bruises, especially in infants and elderly patients. Additionally, the hand may be cupped prior to striking the back or chest of the patient, providing a suction at the point of impact. Such cupping however, can similarly result in bruises and broken bones, and is considered by many to be ineffectual.

Percussion type massagers have also been used to loosen bronchial secretions. In their use, the massager is placed upon the back or the chest of the patient, and the massager is operated such that a vibrating member is forced in and out towards the patient. This percussion-type movement loosens the bronchial secretions, but does not mobilize the secretions to move them out of the congested area.

Another type of massager unit that is used is the oscillation type, in which the vibrating member rotates about an axis perpendicular to the chest or back of the patient when it is applied. This type of unit provides a massaging circular oscillation force to the body but does not give percussion to loosen the secretions so that they may be mobilized. Additionally, the parallel force is in a circular pattern rather than unidirectional.

Percussion-type and oscillation-type massagers have additionally been employed to improve blood circulation. However, these massaging devices do not provide a unidirectional impulse to blood flowing in a vessel and the oscillation-types furthermore have their principle vibratory effect near the surface level of the skin and do not have a substantial effect upon deeper venuous flow. Previously, to improve blood circulation an attendant would wrap his or her hands around a patient's ankle and then move them upward, pressing tightly at the same time, in order to squeeze blood flow in the direction of the heart. This is a very difficult procedure, and strenuous work on the part of the attendant. Alternating pressure belts have been used to provide similar results in leg circulation. The belts consist of a series of air bags wrapped around the patient's leg, each continuously going through the cycle of having pressure increase from the bottom of the leg towards the top, such that there is a squeezing impulse forcing the blood flow up the leg towards the heart. These systems are complex, and requiring difficult synchronization and the total encasement of the patient's legs.

Similar problems arise in the prior art techniques used to relax muscles which have become tense and stiff due to a build-up of lactic acid in the muscle tissue resulting from an inability to rapidly eliminate waste products. Prior art massagers apply percussion or oscillation motion to the muscle, but do not give a continual directional stroke to the muscle to mobilize the waste produces in a direction consistent with the normal direction of blood flow in the muscle.

Regardless of the type of procedure in which these various percussion-type and oscillation type massage unit are employed, these devices all transmit a significant amount of the vibratory energy produced to the hands of the user through the housing Long term exposure to these vibrations on the part of a nurse or attendant using these massagers on a regular basis can result in repetitive motion type injury, including the development of Carpel Tunnel Syndrome. Additionally, the transmission of significant vibrations back through the massage device can reduce the useful service life of the device by producing excessive wear and tear on the bearings associated with the drive motor.

The prior art has attempted to deal with these problems, for example, the device described in U.S. Pat. No. 4,102,334, manufactured by the assignee of the present invention incorporates a transmission cable between the motor drive shaft and the vibrating components, reducing the level of vibration in the motor and housing, but significantly increase the bulk of the device, and often requiring a separate stand or support for the motor housing.

SUMMARY OF THE INVENTION

Among the several objects and advantages of the present invention are:

- The provision of a new and improved massage unit for applying oscillatory motion to a patient's body;
- The provision of the aforementioned massage unit in which the massage unit is a self-contained portable unit;
- The provision of the aforementioned massage unit in which vibrations produced by the oscillatory motion are isolated from the user's hands;
- The provision of the aforementioned massage unit in which a counterweight reduces the vibrations transmitted to the user's hands by counterbalancing an off-center mounting of the oscillating components;
- The provision of the aforementioned massage unit in which the counterweight is located adjacent the off-center mounting to isolated the vibrations of the oscillating components and to reduce multi-axial twisting;
- The provision of the aforementioned massage unit in which the oscillating components are directly driven by a motor output shaft;
- The provision of the aforementioned massage unit in which various adapters may be attached to the oscillating components; and
- The provision of the aforementioned massage unit in which a right-angle adapter may be attached to the oscillating components to produce a percussion-type motion.

Briefly stated, the portable massage unit of the present invention is used for therapeutic purposes such as to loosen and mobilize bronchial secretions in patients, to improve blood circulation, and to relax muscles. The hand-held massage unit includes a vibration-free motor unit having a rotating output shaft directly connected to a vibratory head assembly. The rotational motion of the output shaft is transformed into oscillating orbital motion about the shaft centerline in the adapter portion of the vibratory head assembly by means of an offset cam integrally formed as part of a counterbalanced eccentric. Counterweights within the eccentric reduce the vibrations transmitted to the user's hand and isolate the oscillating vibration of the vibratory head assembly. Undesired rotation of the vibratory head assembly is prevented by means of a rubber boot secured between the oscillating adapter components and a stationary portion of the vibratory head assembly secured to the motor unit. Applicators suitable for various medical need may be secured to the adapter components, including a right-angle applicator capable of converting the oscillating vibrations into a percussion-type motion.

The foregoing and other objects, features, and advantages of the invention as well as presently preferred embodiments thereof will become more apparent from the reading of the following description in connection with the accompanying drawings.

BRIEF DESCRIPTION OF THE DRAWINGS

In the accompanying drawings which form part of the specification.

Corresponding reference numerals indicate corresponding parts throughout the several figures of the drawings.

DESCRIPTION OF THE PREFERRED EMBODIMENT

Figure 1A:
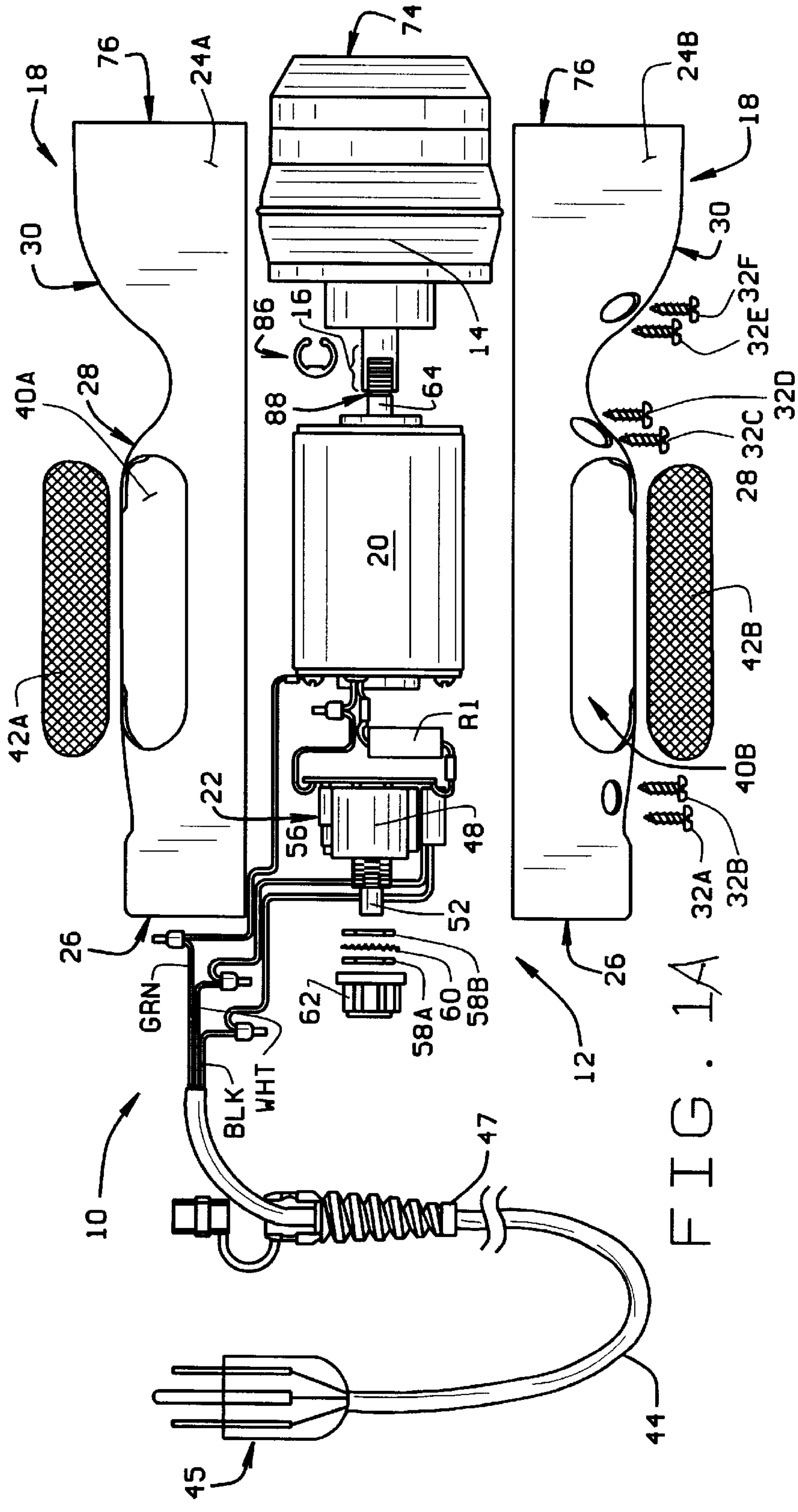
FIG. 1A is an exploded view of the portable hand-held massage unit of the present invention.

The following detailed description illustrates the invention by way of example and not by way of limitation. The description will clearly enable one skilled in the art to make and use the invention, describes several embodiments, adaptations, variations, alternatives, and uses of the invention, including what we presently believe is the best mode of carrying out the invention.

The portable massage unit, generally depicted in the drawings as 10, has components which include a motor assembly 12 and a vibrator head assembly 14. The motor assembly 12 transmits rotary power through a direct coupling 16 to the vibrator head assembly 14 wherein the rotational movement is converted into oscillating orbital motions.

Figure 2B:
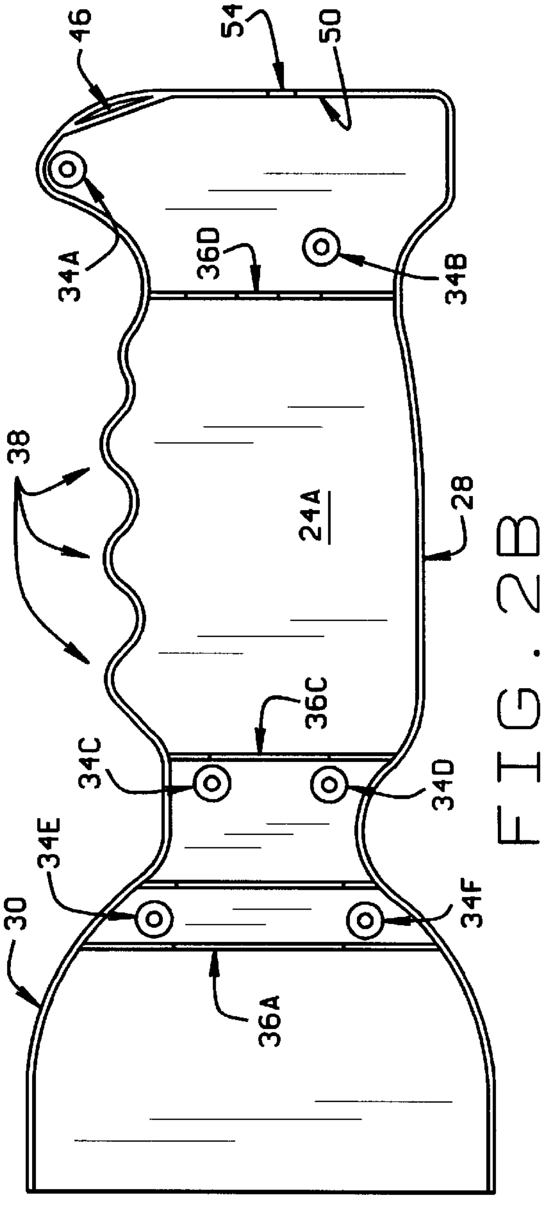
FIG. 2B is a side view of the internal structures of the left side of the motor housing.
Figure 2A:
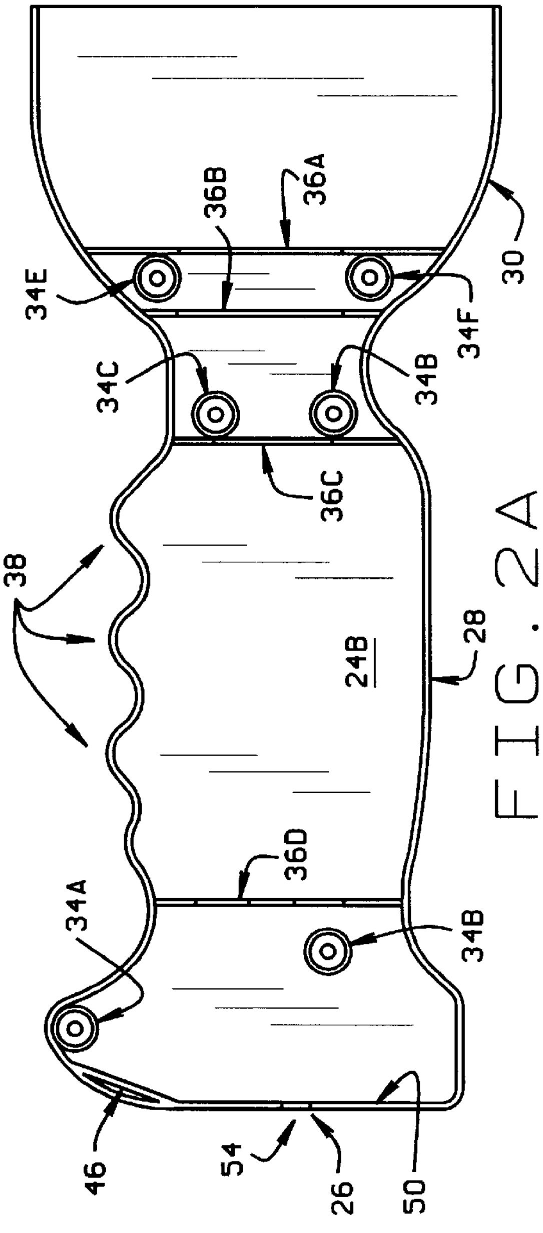
FIG. 2A is a side view of the internal structures of the right side of the motor housing.

The motor assembly 12 includes a motor housing 18 (FIG. 1A) within which is an axially mounted DC motor 20, and a motor control assembly 22. The motor housing 18 is a two-piece injection-molded plastic component, consisting of interlocking left and right sides 24A, 24B, (seen in FIGS. 2A and 2B), and is suitable for gripping by one or two hands. When assembled, the housing 18 comprises a flat base 26, a generally cylindrical body portion 28 enclosing the motor 20, and a bell-shaped adapter enclosure 30 partially surrounding the vibrator head assembly 14. The left and right sides 24A, 24B are secured together in a standard fashion by screws 32A–F passing through matching internal bosses 34A–F. Internal reinforcing ribs 36A–D increase the structural integrity of the housing 18 and retain the motor 20 in a fixed position. Molded into the exterior surface of the body 28, finger grips 38 provide a suitable gripping surface for the user. Formed adjacent the finger grips 38, recesses 40A, 40B receive soft pads 42A, 42B, (FIG. 1A) which aid in reducing vibrational motion transmitted to the user's hands. The soft pads 42A, 42B may be composed of a rubber or silicone material, and are preferably bonded to the body 28 by a suitable adhesive.

Within the housing 18, the motor control assembly 22 regulates the operation of the massage unit 10 by controlling the flow of electrical power to the DC motor 20. Electrical power is received by the motor control assembly 22 through a conducting cable 44, preferably a hospital grade three-line power cord with a standard three-prong adapter 45, entering the motor housing 18 through a cable opening 46 in the base 26. Surrounding the base of the conducting cable 44 as it enters the cable opening 46 is a strain relief 47, adapted to prevent excessive bending or pulling on the cable.

Figure 1B:
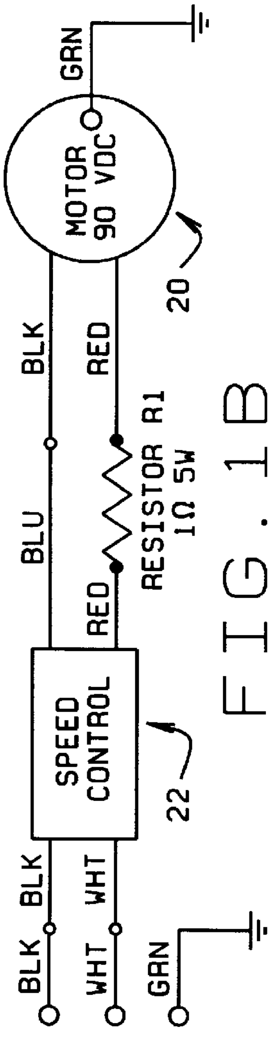
FIG. 1B is a wiring schematic for the electrical connections between the speed control and motor.

As is well known in the art, the motor control assembly 22 includes a voltage varying potentiometer 48 and associated circuitry to regulate the electrical power distributed to the motor 20 (FIG. 1B). The potentiometer 48 is positioned adjacent the inner surface 50 of the base 26 such that a rotating control shaft 52 protrudes through an opening 54 in the base 26. As best shown in FIG. 1, a concentric threaded sleeve 56 surrounds the lower portion of the control shaft 52 to receive nuts 58A, 58B and a lock washer 60. Nut 58A and washer 60 are threaded over the sleeve 56 prior to the positioning of the potentiometer 48 such that the nut 58A may be tightened to clamp the lock washer 60 against the inner surface of the base 26 after the potentiometer 48 is fitted within the housing 18. Nut 58B, threaded onto the control shaft 52 after it is properly positioned, it tightened directly against the outer surface of the base 26, clamping the control shaft 52 and potentiometer 48 securely to the housing 18.

The operation of the motor 20 is regulated through a control knob 62 press fitted onto the protruding portion of the control shaft 52. Rotation of the control knob 62 correspondingly rotates the control shaft 52, altering the voltage levels within the potentiometer 48. The operational speed of the motor 20 is directly proportional to the potentiometer voltage levels, hence rotation of the control knob 62 in an increasingly "on" direction increases the potentiometer voltage and correspondingly the rotational speed of a threaded output shaft 64 of the motor 20. The rotation motion of the motor output shaft 64 is in turn transmitted directly to the components of the vibrator head assembly 14 mounted within the bell-shaped adapter enclosure 30.

Figure 8:
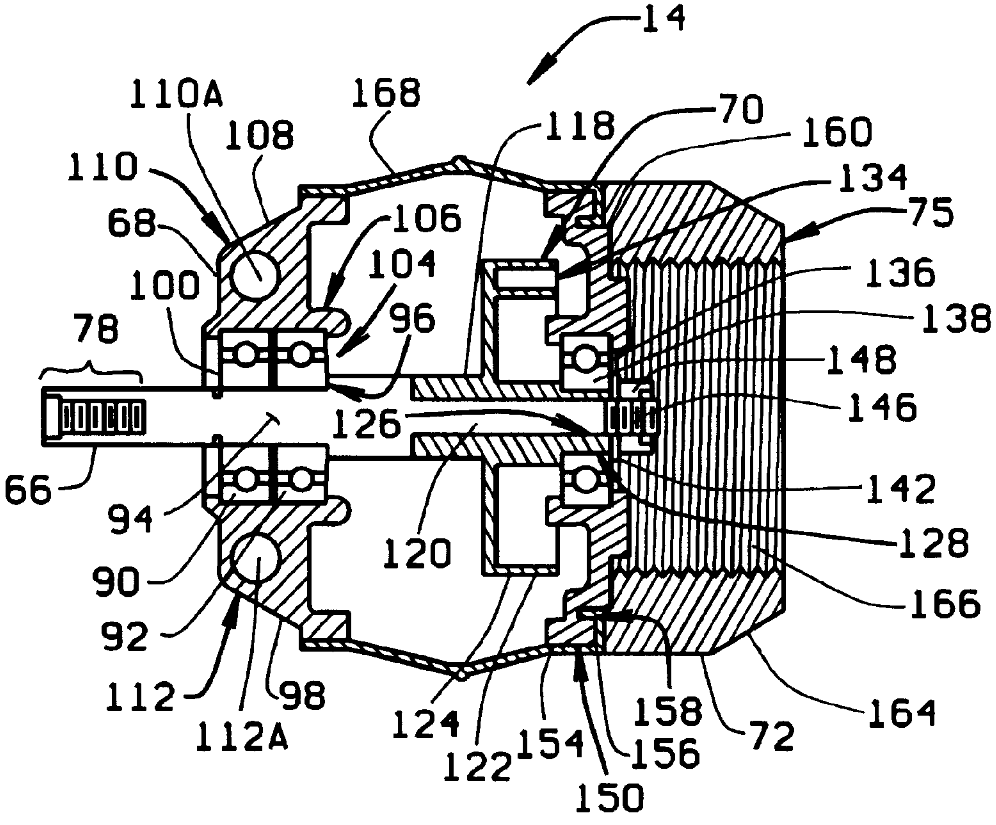
FIG. 8 is a side sectional illustration of the assembled vibrator head assembly.

The vibrator head assembly 14 (FIG. 8) includes a driveshaft 66, a back bearing plate 68, a counterbalanced eccentric 70, and a front bearing plate 72. As shown in FIGS. 1 and 8, the output shaft 64 and the drive shaft 66 define a direct drive connection for the head assembly 14. The vibrator head assembly 14 is assembled around the driveshaft 66, and fitted with the adapter enclosure 30 such that the forward end 74 of the head assembly 14 extends beyond the forward edge 76 of the housing 18. The driveshaft 66 axially traverses the vibrator head assembly 14, and includes a fitted tip 78 axially aligned with the threaded motor output shaft 64. The fitted tip 78 of the driveshaft 66 includes a recessed shoulder 80, sized to fit over a non-threaded portion of the motor output shaft 64, and a smaller-diameter inner threaded bore 82, with threads 84 corresponding to the threads on the threaded portion of the motor output shaft 64. The vibrator head assembly 14 is secured to the motor output shaft 64 by threading the fitted tip 78 onto the output shaft 64 until the threaded portion of the shaft is fully seated within the threaded bore 82. A "C" clip 86 is then fitted within an annular recess 88 on the motor output shaft 64, securing the vibrator head assembly. Rotational motion of threaded motor output shaft 64 is directly transferred to the fitted tip 78 and driveshaft 66 through the threaded connection.

Positioned directly forward of the fitted tip 78, the inner races of bearings 90 and 92 are press-fitted around a bearing support portion 94 of the driveshaft 66. The inner race of bearing 92 additionally rests against a shoulder 96 formed against the rearward edge of the driveshaft center portion 98. A circumferential groove 100 adjacent the rearward end of the bearing support 94 receives a snap ring 102 which retains bearings 90 and 92 in position on the bearing support 94.

Figure 3A:
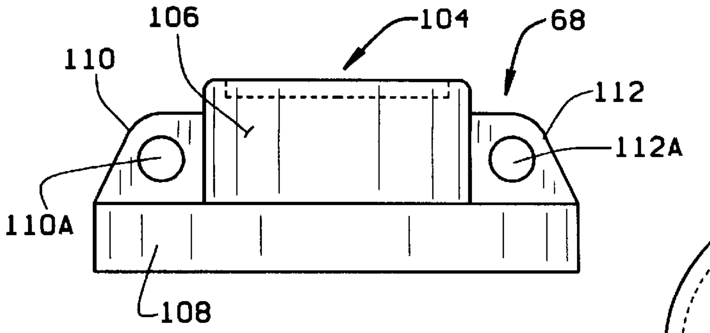
FIG. 3A is a side illustration of the back bearing plate.
Figure 3B:
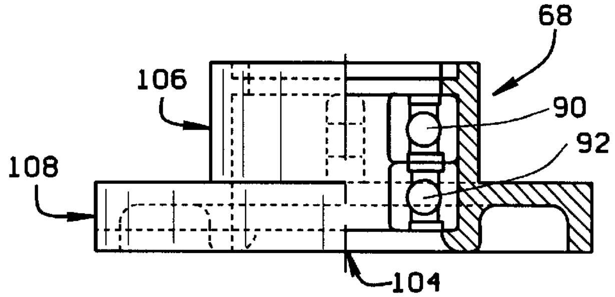
FIG. 3B is a side sectional view of the back bearing plate of FIG. 3A.
Figure 3C:
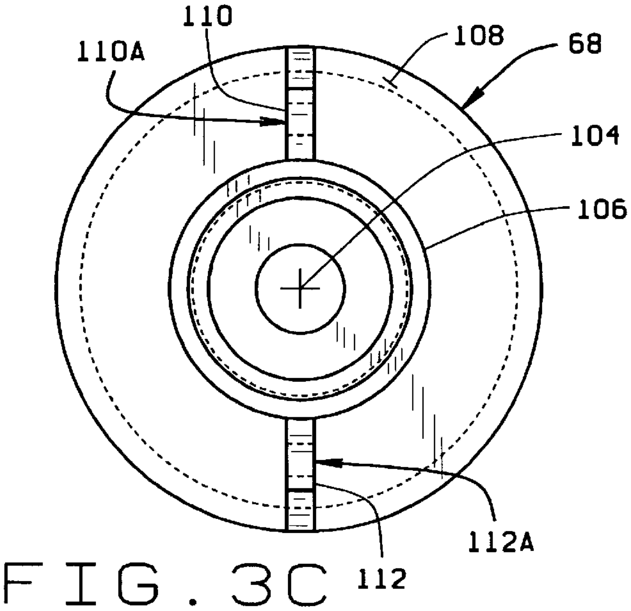
FIG. 3C is a top view of the back bearing plate of FIG. 3B.

The back bearing plate 68 shown in FIGS. 3A–3C has an axially located central bore 104, which is press fitted around the outer races of bearings 90 and 92. As is shown in FIG. 3, the back bearing plate 68 includes a cylindrical body 106, and an enlarged annular flange 108 extending perpendicular to the axis of rotation of the drive shaft 66. Mounting tabs 110 and 112 are integrally molded perpendicular between the body 106 and flange 108, on opposite sides of the central bore 104. Each mounting tab 110, 112 includes a bracket hole 110A, 112A sized to press-fit around a reduced diameter end 114 of an internal boss 34A, 34B adjacent the bell-shaped adapter enclosure 30. When assembled, screws 32A, 32B passing through internal bosses 34A, 34B secure the back bearing plate 68 in a fixed position relative to the housing 18. The back bearing plate 68 correspondingly supports the driveshaft 66.

Figure 4A:
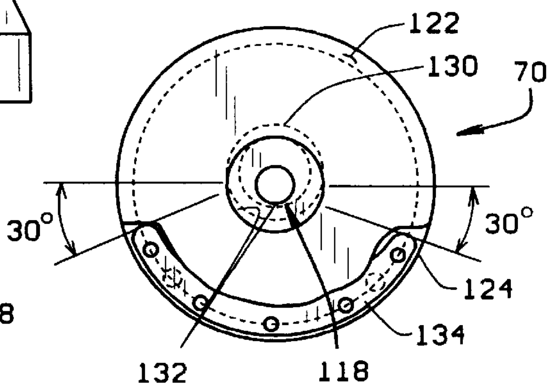
FIG. 4A is a top view of the counterbalanced eccentric.
Figure 4B:
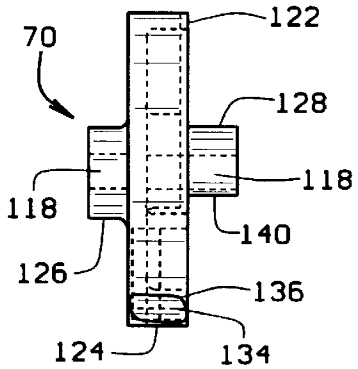
FIG. 4B is a side view of the counterbalanced eccentric of FIG. 4A.

Forward of the bearings 90 and 92, the center portion 98 of the drive shaft 66 serves as a spacer between the forwardmost bearing 92 and the counterbalanced eccentric 70. The counterbalanced eccentric 70, shown in FIGS. 4A–4B, is formed from molded plastic, and includes a semi-cylindrical axial bore 118 which is press-fitted around a longitudinally flattened key portion 120 of the drive shaft 66. The interlocking between the semi-cylindrical axial bore 118 and the flattened key portion 120 prevents the eccentric 70 from rotating relative to the drive shaft 66. Essentially dish shaped, the eccentric 70 includes a forward-facing flange 122 along the outer circumference 124, and both a rear sleeve 126 extending axially rearward around the drive shaft 66, and an integrally molded offset cam 128 extending forward around the flattened key portion 120. The integral offset cam 128 is positioned such that the point of greatest offset 130 is orientated on the opposite side of the drive shaft 66 from the flattened face 132 of the key portion 120 as best seen in FIG. 4A. An arcuate shaped counterbalance weight 134 is integrally secured within a depression 136 in the forward facing flange 122, spanning an arc of approximately 120 degrees and centered perpendicular to the flattened face 132 as best seen in FIG. 4A. The counterbalance weight 134 is preferably composed of a dense material, such as lead, and produces a flywheel effect enhancing the performance of the motor 20 and minimizing the vibrations transferred along the drive shaft 66. The counterbalance weight 134 does not extend beyond the outer circumference 124 of the eccentric 70.

Figure 6A:
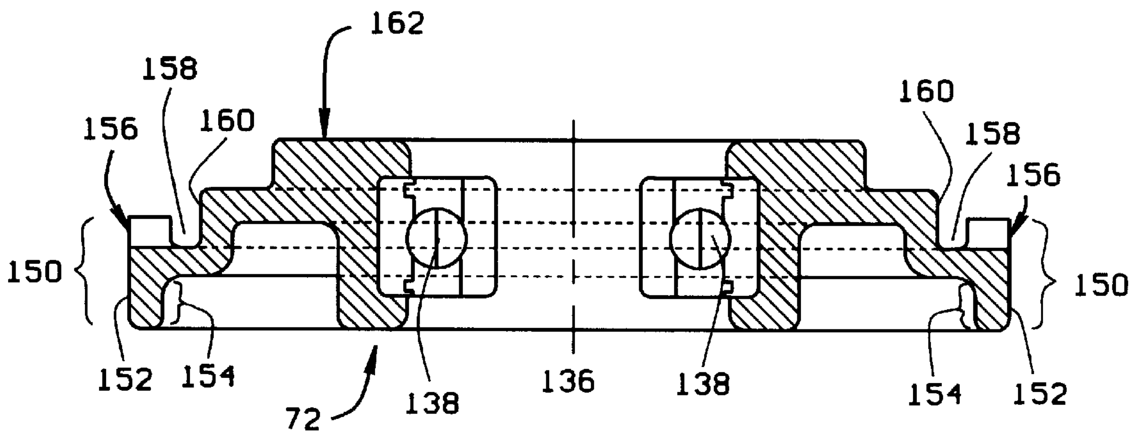
FIG. 6A is a side sectional view of the front bearing plate.
Figure 7:
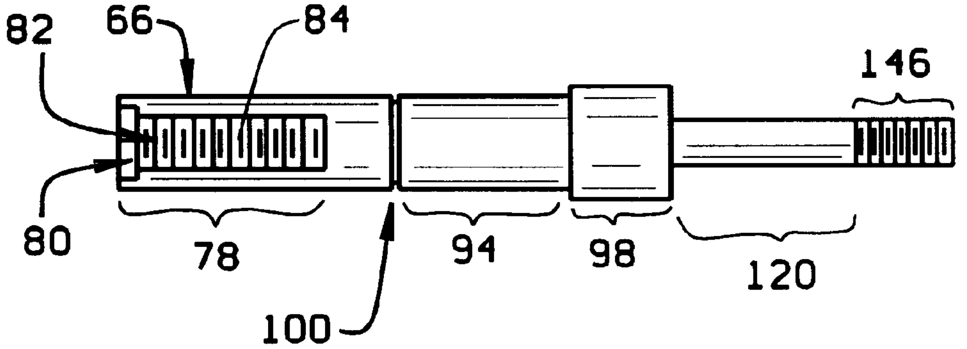
FIG. 7 is a perspective view of the driveshaft.

Positioned forward and around the outer circumference 124 of eccentric 70, the front bearing plate 72 shown in FIG. 6A, is symmetrical in design, and includes an axial cylindrical bore 136 which receives the outer race of bearing 138 by a press-fit. The inner race of bearing 138 is press-fitted around the outer circumference 140 of the offset cam 128, such that the front bearing plate 72 is fitted directly adjacent the forward surface of the eccentric 70. As seen in FIG. 8, the forward portions of the inner and outer races of bearing 138 are supported by a washer 142 with an offset bore 144 fitted over a threaded end 146 of the drive shaft 66. A castle-nut 148 is threaded and locked onto the threaded end 146, securing the washer 142 against the forward bearing plate 72 and holding the bearing 138 firmly against the eccentric 70.

Figure 5A:
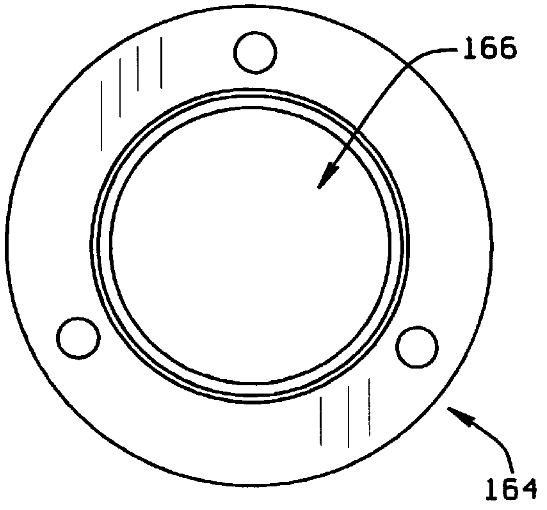
FIG. 5A is a bottom view of the adapter ring.
Figure 5B:
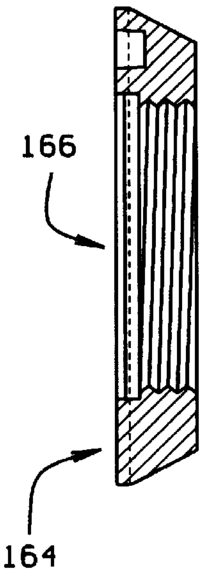
FIG. 5B is a side sectional view of the adapter ring of FIG. 5A.

The forward bearing plate 72, being mounted about the bearing 138 and the offset cam 128 is therefore eccentrically mounted such that rotation of the drive shaft 66 and eccentric 70 causes the forward bearing plate 72 to oscillate in an orbital motion. The forward bearing plate 72 includes an annular flange 150 extending both forward and rearward along the outer circumference 152 of the bearing plate 72. The rearward projection 154 of the annular flange 150 surrounds an longitudinal portion the outer diameter of the eccentric 70 with sufficient clearance to avoid contact during the oscillating motion of the forward bearing plate 72. The forward portion 156 of the annular flange 150 defines an annular groove 158 between the flange 150 and a shoulder 160 formed in the forward surface 162 of the bearing plate 72. A threaded adapter ring 164 shown in FIGS. 5A–5B, having a large diameter axially threaded bore 166 is press fitted within the annular groove 158 and bonded to the forward bearing plate 72. The adapter ring 164 provides a threaded connection point for the various massage attachments (not shown).

The portion of the annular flange 150 extending rearward from the forward bearing plate 72 additionally serves as a forward mounting point for an open-ended cylindrical rubber boot 168. The rubber boot 168 is secured to the outer circumference of both the forward plate annular flange 150 and the back plate annular flange 108. As thus described, the oscillating member is secured to the housing along the back plate or support through the rubber boot 168. The rubber boot 168 stabilizes the vibrator head assembly 14, and prevents circular rotation of the forward bearing plate 72 relative to the secured back bearing plate 68, while including sufficient elastic characteristics to permit the forward bearing plate 72 to oscillate in an orbital motion relative to the back bearing plate 68.

In operation, the portable massage unit 10 can be gripped about the housing 18 with one or two hands. Preferably, only one hand is needed, and the unit 10 can thus be held by either an attendant or by an individual patient such that the various massage adapters (not shown) threaded to the adapter ring 164 are in contact with a part of the body, such as the chest, in the position desired. With the control knob 62 in an "on"

position, the rotation of the motor 20 is transmitted directly to the vibrator head assembly 14 through the locking sleeve 80 from the output shaft 64 to the driveshaft 66. Axial support of the driveshaft 66 is provided by the bearings 90 and 92 which are held in position within the central bore 104 of the secured back bearing plate 68.

The rotation of the driveshaft 66 in turn rotates the eccentric 70 secured forward of the back bearing plate 68. The offset cam 128 on the forward surface of the eccentric traverses an orbital path during the rotation of the eccentric 70. Correspondingly, the forward bearing plate 72 fitted on bearing 138 around the offset cam 128 oscillates in an orbital motion. A massage adapter threaded onto the adapter ring 164 will oscillate in the same orbital motion as the forward bearing plate.

As the portable massage unit 10 and massage adapter are moved inward towards and across the body surface, the massage adapter thereby imparts to the patient and angular force produced by both perpendicular and parallel components with respect to the body surface to which the massage adapter is applied. This movement imparts a percussive force against the patient's body as well as a directional stroking force across the surface of the body. The directional stroke depends upon the direction of the orbital movement of the massage adapter, and in the direction that the adapter moves across the body.

The percussive force of the massage adapter acts to loosen bronchial secretions while the directional force has the effect of mobilizing the secretions in the direction of the directional stroke. The massage unit 10 can thus be placed against the torso in selected positions to mobilize bronchial secretions away from an area in a chosen direction.

The portable massage unit may also be used to improve blood circulation in parts of the body such as the legs. In this case, the massage adapter is placed along the leg at a location where improved circulation is desired such that the massage adapter will have a directional stroke in the direction in which increased blood flow is desired. While the offset cam 128 oscillates in the vibrator head 14, the forward bearing plate 72 and attached massage adapter impart a force to the blood vessels so that the blood is forced in the preselected direction through the blood vessels. Thus, the massage unit 10 can be placed to propel blood from the legs towards the heart, or toward another body area.

During the operation of the portable massage unit 10, the bell-shaped adapter enclosure 30 of the housing 18 acts to prevent the hands or other body parts from being harmed by any of the moving parts of the massage unit 10. Additionally, the soft pads 42A, 42B on the exterior of the body 28 and the counterweight 134 in the eccentric 70 act to isolate the user's hands from the vibratory motions produced by the offset cam 128. Substantially reducing the vibrations transmitted through the direct connection between the driveshaft 66 and the motor output shaft 64 correspondingly reduces the risk of repetitive motion injury to the user.

The various massage adapters which may be threaded onto the adapter ring 164 may include a variety of shapes and sized, each specifically designed to provide oscillating and percussion forces at varying intensities to various parts of the body. Massage adapters may be quickly and easily interchanged by simply unscrewing the current massage adapter from the adapter ring 164 and screwing in another massage adapter having the desired characteristics.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

What is claimed is:

1. A portable, self-contained, hand-held massage apparatus for use in the therapeutic application of repetitive force to a patient, comprising:

a housing suitable for gripping by a human, the housing having a longitudinal axis;

a motor having a output shaft, the motor being mounted axially within the housing, the output shaft extending forward along the direction of the longitudinal axis of the housing;

an oscillating member mounted within the housing directly attached to the output shaft of said motor, said oscillating member translating rotary motion of the output shaft into orbital oscillations, said oscillating member being vibrationally isolated from said housing, said oscillating member including an axial drive shaft, said oscillating member including;

a back support in said housing and mounted about said axial drive shaft, said back support supporting said drive shaft on at least one bearing structure;

a counter balance eccentric axially secured to said drive shaft forward of said back support, said eccentric having a forward surface and a rear surface, and an integral offset cam protruding from said forward surface, said eccentric surrounding a portion of said drive shaft; and an oscillating plate, said oscillating plate being mounted about said offset cam axially outwardly thereof, said oscillating plate oscillating in an orbital motion upon rotation of said drive shaft.

2. The portable massage apparatus of claim 1 wherein said housing further includes an open forward end, said oscillating member being secured to said housing along said forward end, a portion of said oscillating member extending beyond said forward end.

3. The portable massage apparatus of claim 1 wherein said counter balance eccentric includes a counter balance weight.

4. The portable massage apparatus of claim 3 wherein said counterbalance weight is located axially opposed to a point of maximum axial offset of said offset cam, said counterbalance weight reducing vibrations in said eccentric.

5. The portable massage apparatus of claim 4 wherein the counterbalance eccentric has an outer circumference and the counterbalance weight is secured within the outer circumference of the counterbalance eccentric.

6. The portable apparatus of claim 1 wherein said counterbalance weight is located between the forward and rearward surfaces of said counterbalance eccentric.

7. The portable massage apparatus of claim 1 wherein said oscillating member is secured to said housing along said back support.

8. The portable massage apparatus of claim 7 wherein said oscillating plate is secured against rotation relative to said back support.

9. The portable massage apparatus of claim 1 wherein said oscillating member is adapted to receive a removable massage device.

10. The massage apparatus of claim 1 wherein said motor is an adjustable speed motor.

11. A portable hand-held massage apparatus, comprising:

a housing, the housing having a longitudinal axis:

a motor having an output shaft, the motor being mounted within the housing, the output shaft extending along the direction of the longitudinal axis of the housing;

a head assembly associated with the housing including:

a coupling connected to the output shaft;

a back support mounted in the housing and positioned about said coupling, said back support supporting at least one of said output shaft and said coupling on at least one bearing;

an oscillating member mounted to the housing, said oscillating member being attached to the output shaft of said motor by the coupling which connects said oscillating member to said output shaft, said oscillating member being vibrationally isolated from said housing;

a counterbalance eccentric mounted to said coupling forward of said support, said eccentric having a forward surface and a rearward surface;

an integral offset cam protruding from said forward surface, surrounding a portion of said coupling; and an oscillating plate, said oscillating plate being mounted about said offset cam, said oscillating plate defining a support for said coupling, said oscillating plate moving in orbital, directional motion upon rotation of said coupling.

12. The massage apparatus of claim 11 wherein said counter balance eccentric is integrally formed with said offset cam:

a first support mounted to said housing;

a second support mounted along the drive system in axially spaced relationship to said first support, said first and second supports providing rotational support for said drive system;

a counter balance eccentric attached to said drive system in spaced relationship to said first support, said eccentric having an integral offset cam protruding axially outwardly therefrom, the second support being operatively driven by said offset cam; and a device for mounting a massage applicator axially outwardly of said second support, said motor and said head assembly being arranged along the longitudinal axis of the enclosure.

13. The massage apparatus of claim 12 wherein said output shaft and said coupling are integrally formed with one another.

14. In a massage apparatus having a motor, an applicator for imparting a massage action, and an enclosure housing the motor, the enclosure defining a longitudinal axis, the improvement comprising a system for imparting orbital motion to the massage applicator, the system comprising:

a drive system operatively connected to the motor, said drive system including a shaft;

a head assembly including:

a first support mounted to the enclosure;

a second support mounted along the drive system in axially spaced relationship to said first support, said first and second supports providing rotational support for said drive system;

a counter balance eccentric attached to said drive system in spaced relationship to said first support, said eccentric having an integral offset cam protruding axially outwardly therefrom, the second support being operatively driven by said offset cam; and a device for mounting the massage applicator axially outwardly of said second support, said motor and said head assembly being arranged along the longitudinal axis of the enclosure, said head assembly being vibrationally isolated from said enclosure.

15. The apparatus of claim 14 further including a counterweight mounted about said drive system and opposing a point of maximum axial offset of said eccentric cam.

16. A portable, self-contained, hand-held massage apparatus, comprising:

a housing having a longitudinal axis, said housing including an open forward end;

a motor having an output shaft, the motor being mounted within the housing, the output shaft extending axially forward along the direction of the longitudinal axis of the housing;

an oscillating member directly attached to the output shaft of said motor so as to be driven directly thereby, said oscillating member being secured to said housing along said forward end, a portion of the oscillating member extending beyond said forward end, said oscillating member translating rotary motion of the output shaft into orbital oscillations, said oscillating member being vibrationally isolated from said housing, said oscillating member including an axial drive shaft, a back support mounted about said drive shaft, said back support supporting said drive shaft on at least one bearing, a counter balance eccentric secured to said drive shaft axially forwardly of said back support, said eccentric having a forward surface and a rear surface, an integral offset cam protruding from said forward surface, and a counter balance weight of said counter balance eccentric being located between the forward and rear surfaces of said eccentric, said eccentric surrounding a portion of said drive shaft; and an oscillating plate, said oscillating plate being mounted about said offset cam axially outwardly thereof, said oscillating plate oscillating in an orbital motion upon rotation of said drive shaft, the motor and oscillating member being arranged along the housing.

17. A personal hand-held massage apparatus comprising:

a housing having a longitudinal axis;

a motor having an output shaft, the motor being mounted axially within the housing, the output shaft extending forwardly along the longitudinal axis of the housing;

an oscillating member directly coupled to the output shaft of said motor, said oscillating member translating rotary motion of the output shaft into orbital oscillations, said oscillating member being vibrationally isolated from said housing, said oscillating member including an axial drive shaft;

a back support mounted about said drive shaft, said back support supporting said drive shaft on a plurality of bearings, said oscillating member being secured to said housing by said back support;

a counter balance eccentric axially secured to said drive shaft along a forward end thereof, said eccentric having a forward surface and a rearward surface, and an integral offset cam protruding from said forward surface, said eccentric surrounding a portion of said drive shaft; and an oscillating plate, said oscillating plate being mounted about said offset cam, said oscillating plate oscillating in an orbital motion upon rotation of said drive shaft, at least said motor and said oscillating member being mounted to said housing.

* * * * *